United States Patent
Plahey et al.

(10) Patent No.: US 10,806,842 B2
(45) Date of Patent: Oct. 20, 2020

(54) HYDROPHOBIC FILTERS FOR AIR MANAGEMENT IN DIALYSIS MACHINES

(71) Applicant: Fresenius Medical Care Holdings, Inc., Waltham, MA (US)

(72) Inventors: Kulwinder S. Plahey, Martinez, CA (US); John A. Biewer, Waltham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 149 days.

(21) Appl. No.: 16/126,589

(22) Filed: Sep. 10, 2018

(65) Prior Publication Data

US 2019/0076590 A1    Mar. 14, 2019

Related U.S. Application Data

(60) Provisional application No. 62/557,061, filed on Sep. 11, 2017.

(51) Int. Cl.
*A61M 1/16* (2006.01)
*A61M 1/28* (2006.01)
*A61M 1/36* (2006.01)

(52) U.S. Cl.
CPC ........ *A61M 1/1672* (2014.02); *A61M 1/1603* (2014.02); *A61M 1/166* (2014.02); *A61M 1/28* (2013.01); *A61M 1/287* (2013.01); *A61M 1/288* (2014.02); *A61M 1/1658* (2013.01); *A61M 1/282* (2014.02); *A61M 1/365* (2014.02); *A61M 2205/125* (2013.01); *A61M 2205/126* (2013.01); *A61M 2205/127* (2013.01); *A61M 2205/3368* (2013.01); *A61M 2205/36* (2013.01)

(58) Field of Classification Search
CPC .. A61M 1/1603; A61M 1/1658; A61M 1/166; A61M 1/1672; A61M 1/28; A61M 1/282; A61M 1/287; A61M 1/288; A61M 1/365; A61M 2205/125; A61M 2205/126; A61M 2205/127; A61M 2205/3368; A61M 2205/36

See application file for complete search history.

(56) References Cited

U.S. PATENT DOCUMENTS 6,176,903 B1 * 1/2001 Wamsiedler ........ A61M 1/1658
                                                            210/436
6,929,751 B2    8/2005 Bowman, Jr. et al.
(Continued)

FOREIGN PATENT DOCUMENTS

WO    2012067585 A1    5/2012

OTHER PUBLICATIONS

International Search Report and Written Opinion for application No. PCT/US2018/050236 dated Nov. 29, 2018, 15 pages.

*Primary Examiner* — Pranav N Patel

(57) ABSTRACT

Dialysis systems and methods for operating dialysis machines (e.g., peritoneal dialysis machines) for conducting dialysis treatments, may include a dialysis machine for transferring dialysate to a patient from a dialysate bag, and a warmer pouch for flowing the dialysate through to heat to a predetermined temperature before flowing into the patient. The dialysate may flow from the dialysate bag through the warmer pouch for pumping into the patient via tubing. A filter may be coupled to the warmer pouch, and the filter may be configured to filter out air content from the dialysate.

19 Claims, 6 Drawing Sheets

(56) References Cited

U.S. PATENT DOCUMENTS

| | | | |
|---|---|---|---|
| 7,083,719 B2 | 8/2006 | Bowman, Jr. et al. | |
| 7,871,462 B2 | 1/2011 | Yardimci et al. | |
| 8,226,595 B2 | 7/2012 | Childers et al. | |
| 2004/0019312 A1* | 1/2004 | Childers | A61M 1/288 604/4.01 |
| 2007/0213654 A1* | 9/2007 | Lundtveit | A61M 1/28 604/29 |
| 2008/0200866 A1 | 8/2008 | Prisco et al. | |
| 2009/0084718 A1* | 4/2009 | Prisco | A61M 1/1658 210/151 |
| 2012/0152118 A1* | 6/2012 | Weaver | A61M 1/3627 95/157 |
| 2014/0309584 A1* | 10/2014 | Bluchel | A61M 1/1696 604/28 |

* cited by examiner

HYDROPHOBIC FILTERS FOR AIR MANAGEMENT IN DIALYSIS MACHINES

CROSS-REFERENCE TO RELATED APPLICATIONS

This application claims priority to U.S. Provisional Patent Application Ser. No. 62/557,061, filed Sep. 11, 2017, entitled "Hydrophobic Filters for Air Management in Dialysis Machines," the contents of which application are expressly incorporated by reference herein.

FIELD OF THE DISCLOSURE

The disclosure generally relates to dialysis machines, and more particularly to air management in dialysis systems and methods.

BACKGROUND

Dialysis machines are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, called PD cyclers, are designed to control the entire peritoneal dialysis process so that it can be performed at home, usually overnight, without clinical staff in attendance.

A dialysis machine, such as a peritoneal dialysis machine, may include bags containing a fluid, e.g., a dialysate for patient infusion. In peritoneal dialysis machines, for example, tubing as fluid lines are inserted into an abdomen of a patient for flowing fresh dialysate and removing used dialysate, waste, and excess fluid. In bags containing fresh dialysate, an amount of air may also be present, for example, due to fill levels, osmosis, and/or other conditions. If the dialysis machine draws a combination of dialysate and air (e.g., air bubbles) from one of the bags or elsewhere in the system, the dialysis machine may deliver less than the prescribed volume of dialysate to the patient over the course of the treatment and/or a potentially painful build-up of excess air in the patient may result. For example, air delivered to the patient may result in the patient experiencing discomfort, such as shoulder or abdominal pain. Additionally, dialysate flow may change during treatment, which may result in dialysate being overheated and undeliverable at that temperature to the patient. Other events during treatment may occur as well, which may affect the delivery of dialysate. In some embodiments, a dialysis machine may react to these conditions by alerting the patient via an alarm or other notification, and may pause or even stop the treatment. In some embodiments, in order to continue treatment the dialysis machine may automatically purge the dialysate or combination of dialysate and air, for example, to a drain. Fresh dialysate that is drained due to air volume or temperature, or another condition, may waste an unacceptable amount of dialysate, and may result in the patient not receiving a full prescribed treatment or a treatment time being unnecessarily extended. When a patient receives less than 90% of a dialysate treatment, it may be considered ineffective.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a dialysis system for conducting a dialysis treatment may include a dialysis machine for transferring dialysate to a patient from a dialysate bag, and a warmer pouch for flowing the dialysate through to heat to a predetermined temperature before flowing into the patient. The dialysate may flow from the dialysate bag through the warmer pouch for pumping into the patient via tubing. A filter may be coupled to the warmer pouch, and may be configured to filter out air content from the dialysate.

According to an exemplary embodiment of the present disclosure, a method for conducting a dialysis treatment may include transferring dialysate to a patient from a dialysate bag via tubing, and flowing the dialysate through a warmer pouch to heat the dialysate to a predetermined temperature before flowing into the patient. The dialysate may be pumped so as to flow from the dialysate bag through the warmer pouch into the patient via the tubing. Air content may be filtered from the dialysate by a filter coupled to the warmer pouch.

In various of the foregoing and other embodiments of the present disclosure, the filter may be a hydrophobic filter. The filter may be coupled to an inlet of the warmer pouch, such that the air content may be removable before flowing through the warmer pouch. The filter may include a hydrophobic membrane. A negative pressure chamber may be disposed exterior to the hydrophobic membrane, such that the air content is flowable to the negative pressure chamber from an area of positive pressure in the filter. A second filter may be coupled to an outlet of the warmer pouch. Dialysate may be filtered at an outlet of the warmer pouch by the second filter. The filter may be coupled to the warmer pouch by the tubing connecting to the dialysate bag for transferring the dialysate to the patient. The filter may include a container having an inlet for the dialysate to flow into the container, an outlet for the dialysate to flow out of the container after being filtered, and a membrane for filtering out the air content. The inlet and the outlet may be disposed on a lower portion of the container, and the membrane may be disposed on an upper portion of the container. The inlet may extend further in the container than the outlet.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
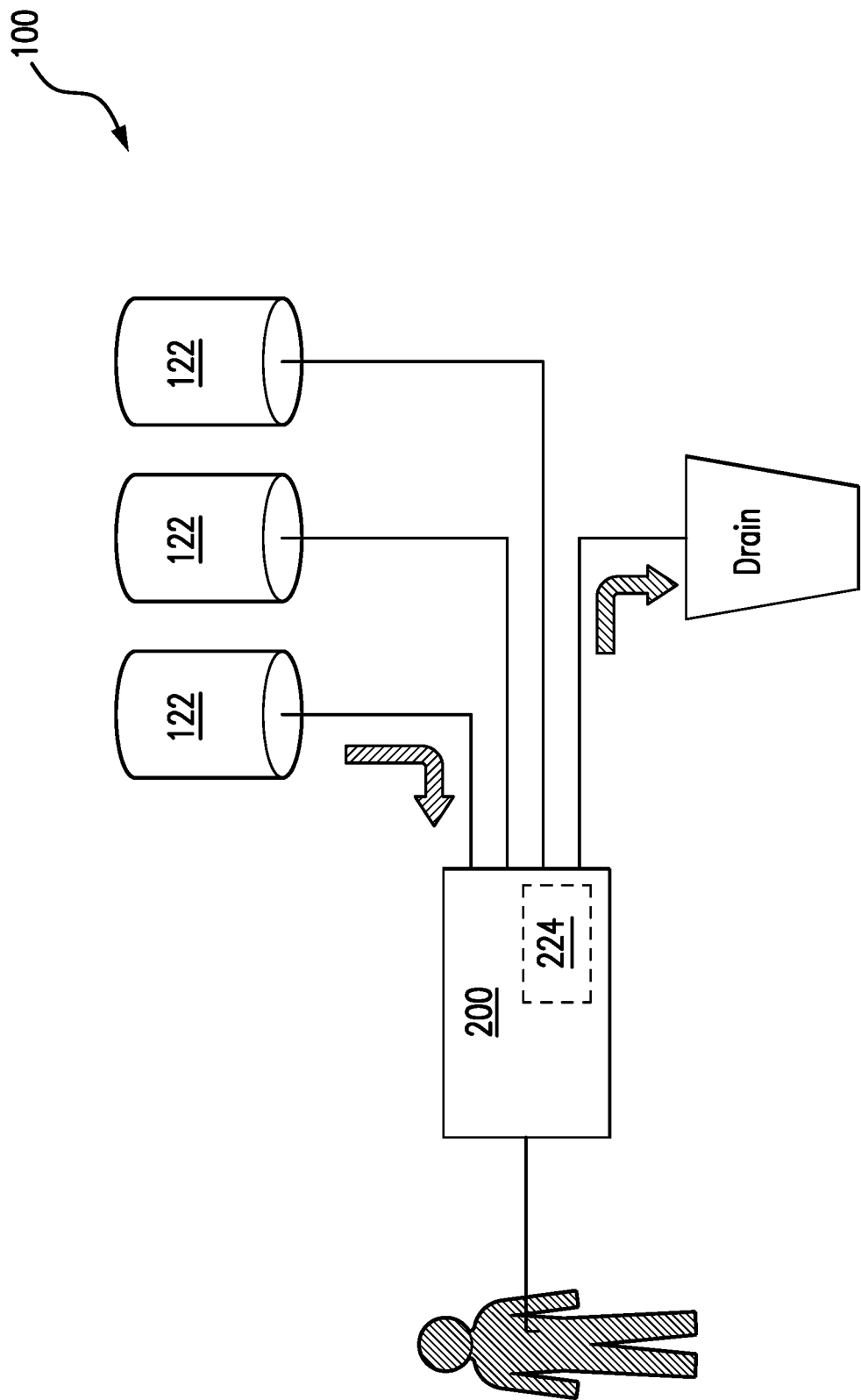
FIG. 1 illustrates an exemplary embodiment of a dialysis system configured in accordance with the present disclosure.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of dialysis machines and of methods for operating dialysis machines may minimize potential dialysate waste, e.g., so a patient may receive a fuller prescribed treatment, treatment times may be efficient, and use of valuable treatment resources may be conserved and optimized to the benefit of the patient, hospital, dialysis centers, environment, etc. As described above, each fluid bag may contain a quantity of air, which may be present as a result of the bag being not completely filled with fluid during manufacture. Additionally, fluid bags may be stored for a period of time prior to sale and/or use by a patient, e.g., 1-2 years or longer. Certain bag materials may be more susceptible to osmosis, for example, a Biofine™ material bag may have a greater amount of air after a period of storage than a bag made of a different material, such as a polyvinyl chloride (PVC) material. For example, a bag may contain a range of approximately 20 cc to 150 cc of air. Although the term "bag" is used throughout, it should be understood that a fluid bag may be any type of container capable of holding a fluid, e.g., a dialysate. In some embodiments, a fluid container may include a container in which dry concentrates are mixed with water to generate dialysate suitable for a dialysis treatment.

To ensure patients safely and efficiently receive the proper amount of dialysis treatment, air in a dialysis machine may be minimized by sensor detection and alarms. Additionally, a dialysis system may be primed, so that at a beginning of a treatment or beginning of delivery from each dialysate bag, prior to delivery of dialysate to a patient, a predetermined amount (e.g., 50 mL to 100 mL) of dialysate may be purged from the system so as to purge any air, for example, air in the tubing and/or a pump cassette and/or initial air bubbles in dialysate bags. When a predetermined volume of air is detected in the dialysate during treatment, or the system is primed, the dialysis machine may be configured to purge or drain waste instead of flowing the dialysate into a patient.

When air is present in the dialysate or system, or another treatment event condition occurs where it is necessary for flow to the patient to be temporarily paused, the dialysate may be unusable for flowing into a patient. When unusable dialysate is dumped via a drain, dialysate that was prescribed to the patient is wasted. Each event of unusable dialysate may result in a range of approximately 30 mL to 100 mL of dialysate being drained instead of flowing into a patient. As one to several events may occur in a single treatment, this wasted dialysate may result in a patient not receiving as full a prescribed treatment as might be possible, and treatment time and use of resources may not be optimal. It may therefore be advantageous as described herein to improve dialysate flow management to minimize dialysate purging when air is present by including a device as part of a dialysis machine, which removes the air from the machine or otherwise allows the air to escape from the machine, e.g., through a filter, without draining or purging solution that would otherwise be usable.

Figure 2:
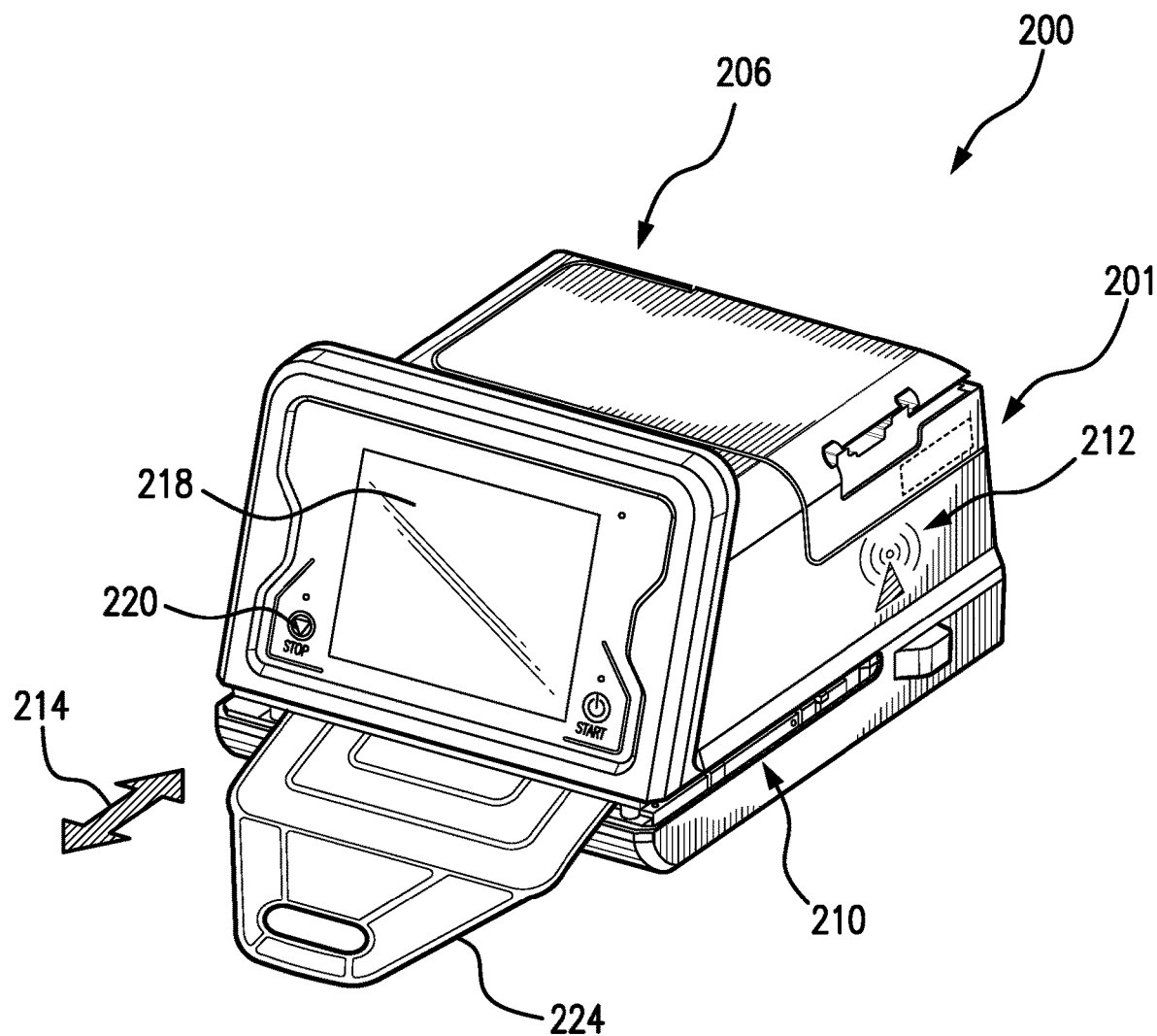
FIG. 2 illustrates an exemplary embodiment of a dialysis machine in the dialysis system of FIG. 1 in accordance with the present disclosure.

Referring to FIGS. 1-2, a dialysis system 100 may include a peritoneal dialysis machine 200, for flowing fresh dialysate into a patient and draining used dialysate out of the patient. During treatment, a volume of dialysate may enter the patient's abdomen and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the used dialysate may be flowed out of the patient's abdomen and purged to a drain connected to the tubing, e.g., the drain line. This exchange of fresh dialysate and used dialysate after a dwell time may occur for several cycles depending on the patient's treatment regimen.

Dialysate bags 122 may be connected to the dialysis machine 200. In some embodiments, hanging the dialysate bags 122 may improve air management as any air is disposed by gravity to a top portion of the dialysate bag 122. Valves may be attached to a bottom portion of the dialysate bags 122 so fluid is drawn out and air delivery is minimized. Dialysate from the dialysate bags 122 may be transferred directly to the patient through a warmer pouch 224. When the dialysate has reached a predetermined temperature (e.g., approximately 98°-100° F., 37° C.) in the warmer pouch 224, the dialysate may be flowed into the patient. The dialysate bags 122 and/or the warmer pouch 224 may be connected to a cartridge, which may be insertable into the dialysis machine 200, via dialysate bag lines and/or warmer pouch line, and the dialysate bag lines may be used to pass dialysate from dialysate bags 122 to the cartridge during use. In addition, a patient line and a drain line may be connected to the cartridge. The patient line may be connected to a patient's abdomen via a catheter and may be used to pass dialysate back and forth between the cartridge and the patient's peritoneal cavity during use. The drain line may be connected to a drain or drain receptacle and may be used to pass dialysate from the cartridge to the drain or drain receptacle during use.

FIG. 2 illustrates an exemplary embodiment of a dialysis machine 200 in dialysis system 100 in accordance with the present disclosure. The dialysis machine 200 may be implemented in the dialysis system 100 and may include, for example, a housing 206, a processing module 201, a connection component 212, a touch screen 218, and a control panel 220 operable by a user (e.g., a caregiver or a patient) to allow, for example, set up, initiation, and/or termination of a dialysis treatment.

The touch screen 218 and the control panel 220 may allow a user to input various treatment parameters to the dialysis machine 200 and to otherwise control the dialysis machine 200. In addition, the touch screen 218 may serve as a display. The touch screen 218 may function to provide information to the patient and the operator of the dialysis system 100. For example, the touch screen 218 may display information related to a dialysis treatment to be applied to the patient, including information related to a prescription.

The dialysis machine 200 may include a processing module 201 that resides inside the dialysis machine 200, the processing module 201 being configured to communicate with the touch screen 218 and the control panel 220. The processing module 201 may be configured to receive data from the touch screen 218 the control panel 220 and sensors, e.g., air, temperature and pressure sensors, and control the dialysis machine 200 based on the received data. For example, the processing module 201 may adjust the operating parameters of the dialysis machine 200. In some embodiments, the processing module 201 may be an MPC823 PowerPC device manufactured by Motorola, Inc.

The dialysis machine 200 may be configured to connect to a network. The connection to network may be via a wired and/or wireless connection. The dialysis machine 200 may include a connection component 212 configured to facilitate the connection to the network. The connection component 212 may be a transceiver for wireless connections and/or other signal processor for processing signals transmitted and received over a wired connection. Other medical devices (e.g., other dialysis machines) or components may be configured to connect to the network and communicate with the dialysis machine 200.

One or more heating elements may be disposed internal to the machine 200. For example, a warmer pouch 224 may be insertable into an opening 210 in a direction indicated at arrow 214. In embodiments, the warmer pouch 224 may be configured so dialysate may continually flow through the warmer pouch 224 to achieve a predetermined temperature before flowing into the patient. For example, in some embodiments the dialysate may continually flow through the warmer pouch 224 at a rate of approximately 200 mL/min. Internal heating elements (not shown) may be positioned above and/or below the opening 210, so that when the warmer pouch 224 is inserted into the opening 210, the one or more heating elements may affect the temperature of dialysate flowing through the warmer pouch 224. In some embodiments, an internal warmer pouch may instead be a portion of tubing in the system that is passed by, around, or otherwise configured with respect to, a heating element(s). In some embodiments, a dialysis machine 200 may provide an active measurement of the dialysate temperature in dialysate bags and/or warmer pouches, e.g., in the dialysate bags 122, and the warmer pouch 224 of FIGS. 1-2. It is understood that FIGS. 1-2 illustrate dialysate continuously flowing through the warmer pouch 224 "in-line" with the dialysis machine 200, reaching an acceptable temperature by the application of internal heating elements.

As described above, embodiments having an in-line warmer pouch 224 may be susceptible to temperature variation of the dialysate. For example, if flow rate changes during treatment, such as a kink in the tubing occurring or an obstruction on the inlet side of the pouch or air content in the dialysate affecting the heating time of the dialysate, dialysate may reach a higher than intended temperature before flowing into the patient. If dialysate is higher than approximately 41° C., or 105° F.-106° F., it may not be delivered to the patient due to safety concerns.

Figure 3:
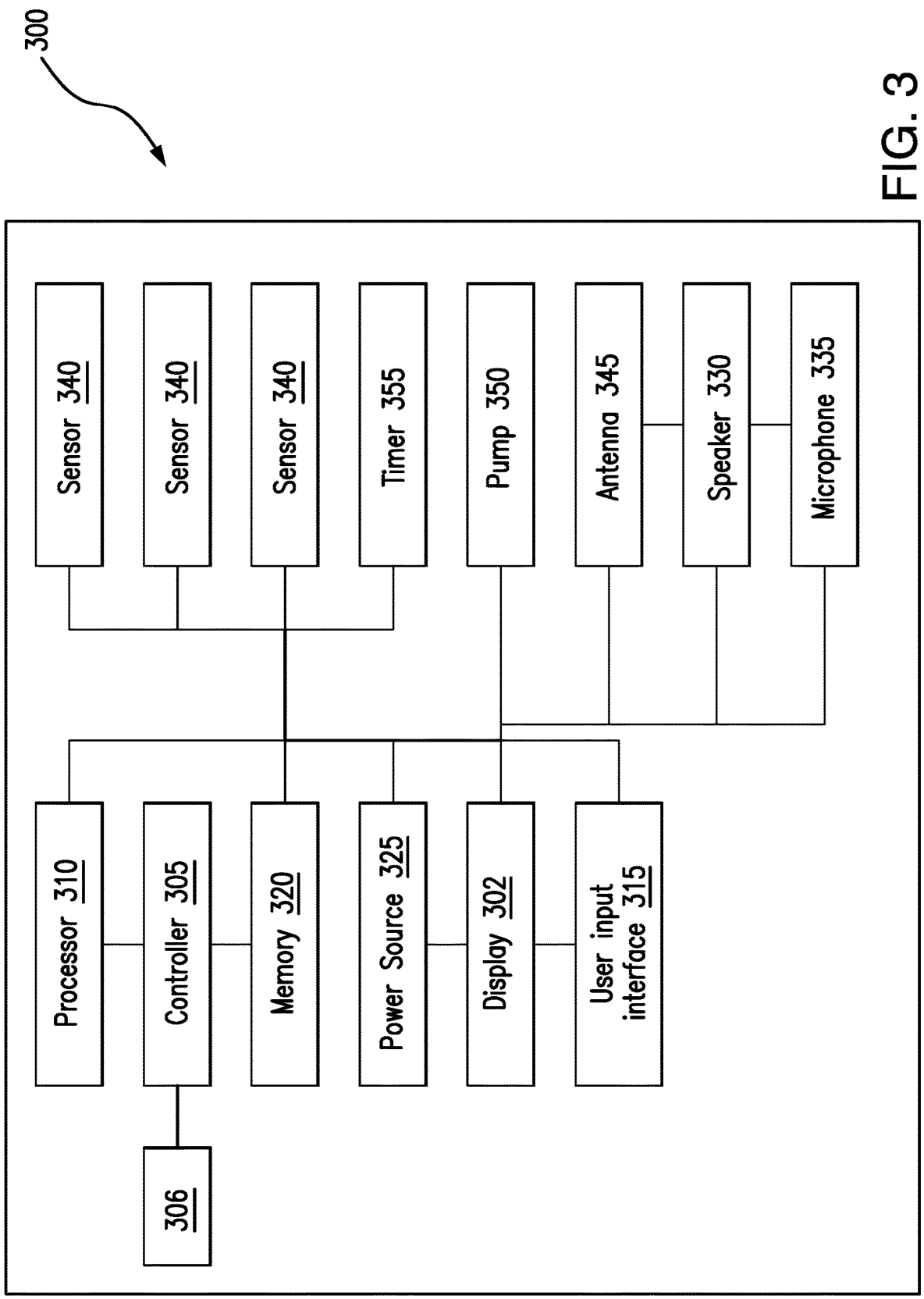
FIG. 3 is a block diagram illustrating an exemplary embodiment of a dialysis machine controller in accordance with the present disclosure.

Referring to FIG. 3, a schematic of an exemplary embodiment of a dialysis machine 300 and a controller 305 in accordance with the present disclosure are shown. The machine 300 may be a home dialysis machine, e.g., a peritoneal dialysis machine, for performing a dialysis treatment on a patient, and may be included in the system 100 described above with respect to FIGS. 1-2 and dialysis machine 200. The controller 305 may automatically control execution of a treatment function during a course of dialysis treatment. The controller 305 may be operatively connected to sensors 340 and deliver a signal to execute a treatment function (e.g., transferring dialysate from the dialysate bag 122 through the warmer pouch 224 and then to the patient), or a course of treatment associated with various treatment systems. In some embodiments, a timer 355 may be included for timing triggering of sensors 340.

In some embodiments, the controller 305, processor 310, and/or memory 320, or combinations thereof of the machine 300 may receive sensor 340 signals indicating a dialysate air content. Each fluid bag (e.g., the dialysate bags 122) may contain an approximate amount of dialysate, such that "approximate amount" may be defined as a 3 L fluid bag containing 3000 to 3150 mL, a 5 L fluid bag containing 5000 to 5250 mL, and a 6 L fluid bag containing 6000 to 6300 mL. The controller 305 may also detect connection of all fluid bags 122 connected. As described above, each fluid bag 122 may contain some amount of air, which may change over time.

Communication between the controller 305 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In embodiments, the dialysis machine 300 may include at least one pump 350 operatively connected to the controller 305. During a treatment operation, the controller 305 may control the pump 350 for pumping fluid, e.g., fresh and spent dialysate, to and from a patient. The pump 350 may also pump dialysate from the dialysate bag 122 through the warmer pouch 224. The controller 305 may also be operatively connected to a speaker 330 and a microphone 335 disposed in the machine 300. The user input interface 315 may include a combination of hardware and software components that allow the controller 305 to communicate with an external entity, such as a patient or other user. These components may be configured to receive information from actions such as physical movement or gestures and verbal intonation. In embodiments, the components of the user input interface 315 may provide information to external entities. Examples of the components that may be employed within the user input interface 315 include keypads, buttons, microphones, touch screens, gesture recognition devices, display screens, and speakers. The machine 300 may also be wirelessly connectable via the antenna 345 for remote communication.

As shown in FIG. 3, sensors 340 may be included for monitoring parameters and may be operatively connected to at least the controller 305, processor 310, and/or memory 320, or combinations thereof. The processor 310 may be configured to execute an operating system, which may provide platform services to application software, e.g., for operating the dialysis machine 300. These platform services may include inter-process and network communication, file system management and standard database manipulation. One or more of many operating systems may be used, and examples are not limited to any particular operating system or operating system characteristic. In some examples, the processor 310 may be configured to execute a real-time operating system (RTOS), such as RTLinux, or a non-real time operating system, such as BSD or GNU/Linux.

According to a variety of examples, the processor 310 may be a commercially available processor such as a processor manufactured by INTEL, AMD, MOTOROLA, and FREESCALE. However, the processor 310 may be any type of processor, multiprocessor or controller, whether commercially available or specially manufactured. For instance, according to one example, the processor 310 may include an MPC823 microprocessor manufactured by MOTOROLA.

The memory 320 may include a computer readable and writeable nonvolatile data storage medium configured to store non-transitory instructions and data. In addition, the memory 320 may include a processor memory that stores data during operation of the processor 310. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 320 may include executable programs or other code that may be executed by the processor 310. The instructions may be persistently stored as encoded signals, and the instructions may cause the processor 310 to perform the functions described herein. The memory 320 may include information that is recorded, on or in, the medium, and this information may be processed by the processor 310 during execution of instructions. The memory 320 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 305.

A pressure sensor may be included for monitoring fluid pressure of the machine 300, although the sensors 340 may also include any of a heart rate sensor, a respiration sensor, a temperature sensor, a weight sensor, an air sensor, a video sensor, a thermal imaging sensor, an electroencephalogram sensor, a motion sensor, audio sensor, an accelerometer, or capacitance sensor. It is appreciated that the sensors 340 may include sensors with varying sampling rates, including wireless sensors.

The controller 305 may be disposed in the machine 200, 300 or may be coupled to the machine 200, 300 via a communication port or wireless communication links, shown schematically as communication element 306 (see FIG. 3). According to various examples, the communication element 306 may support a variety of one or more standards and protocols, examples of which include USB, WiFi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 300, the controller 305 may be operatively connected to any of the sensors 340, pump 350, and the like. The controller 305 may communicate control signals or triggering voltages to the components of the machine 300. As discussed, exemplary embodiments of the controller 305 may include wireless communication interfaces. The controller 305 may detect remote devices to determine if any remote sensors are available to augment any sensor data being used to evaluate the patient.

Figure 4:
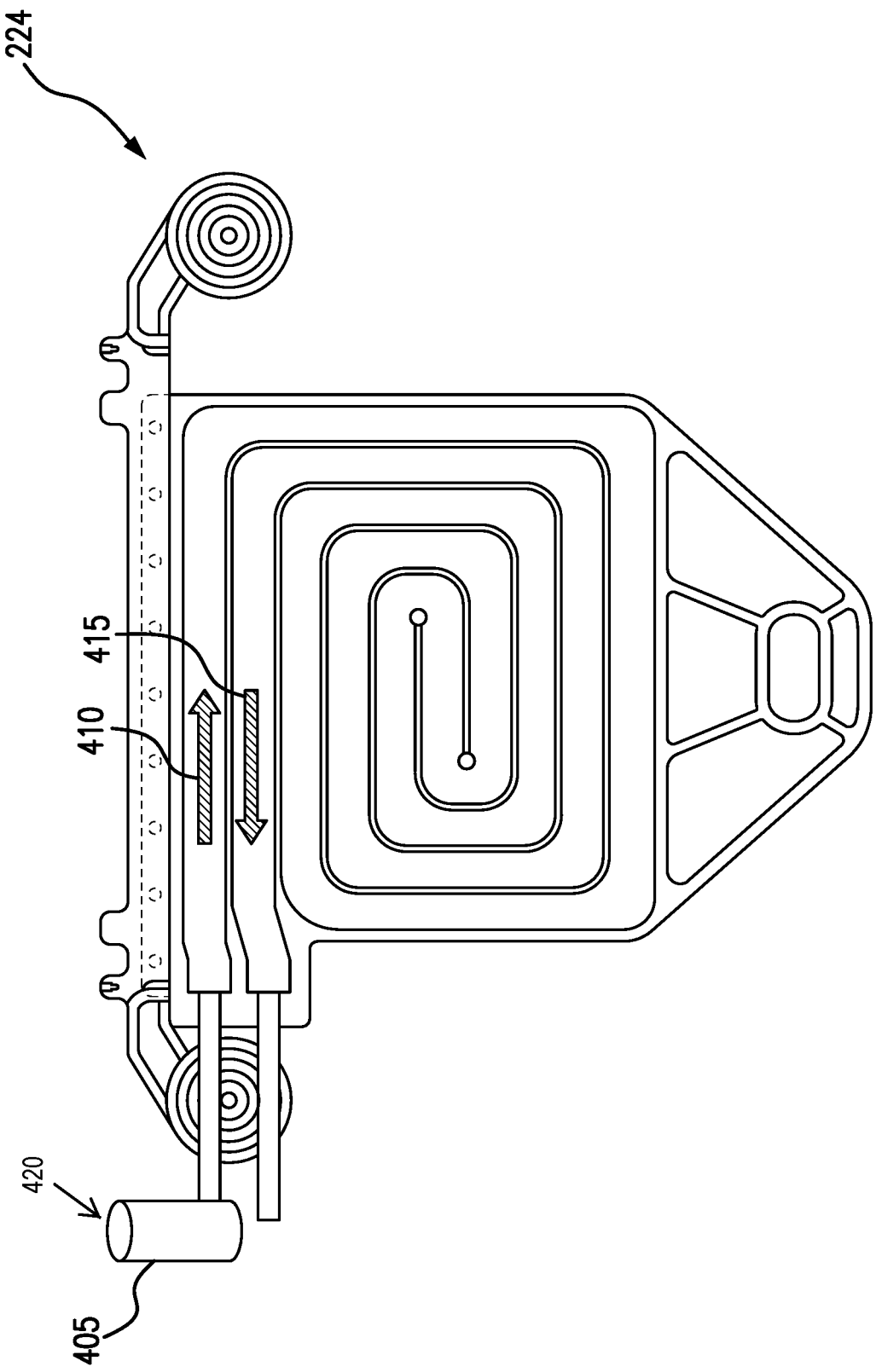
FIG. 4 illustrates an exemplary embodiment of a warmer pouch for the dialysis system of FIG. 1 in accordance with the present disclosure.
Figure 5:
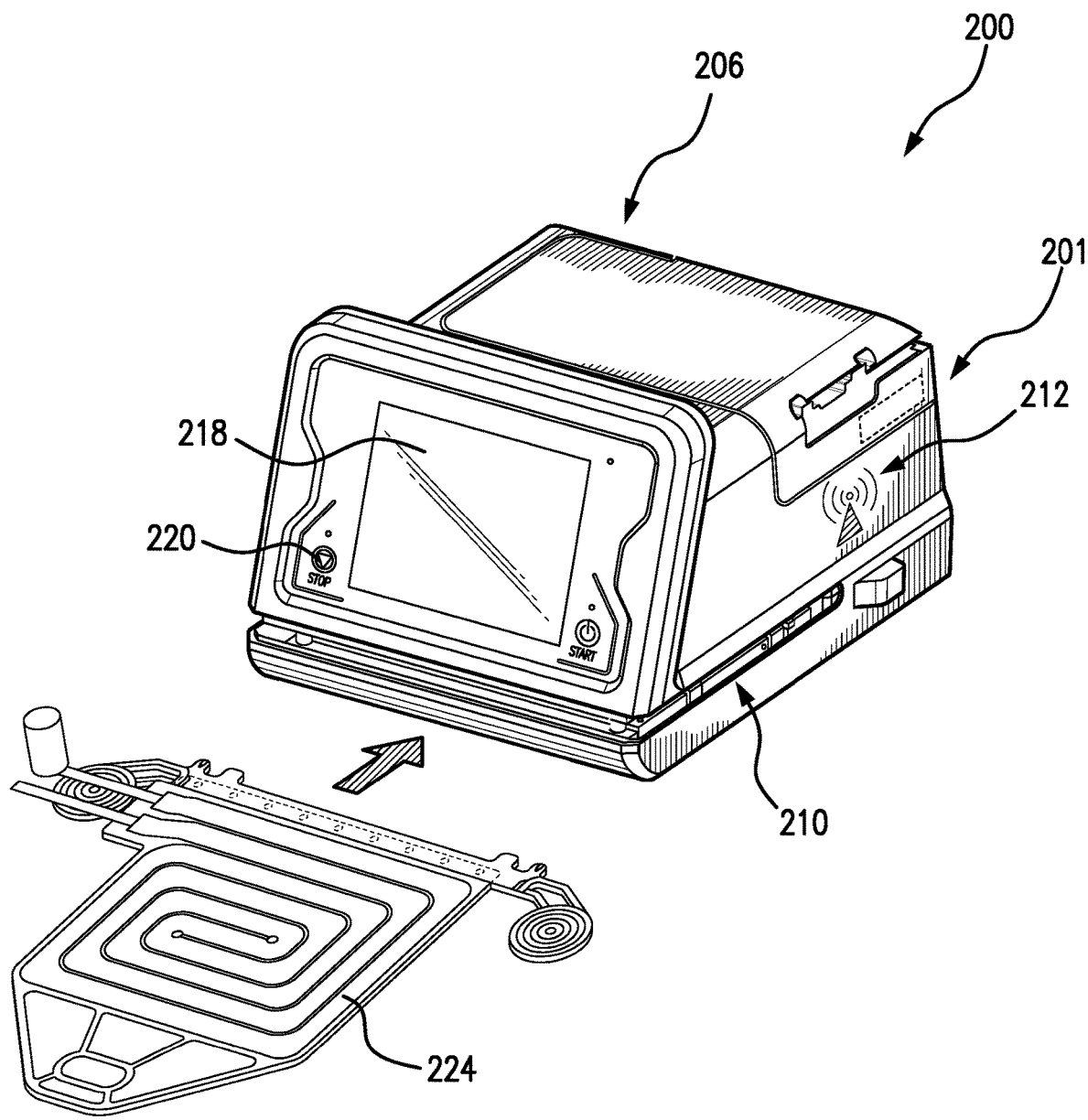
FIG. 5 illustrates an exemplary embodiment of a dialysis system configured in accordance with the present disclosure.
Figure 6:
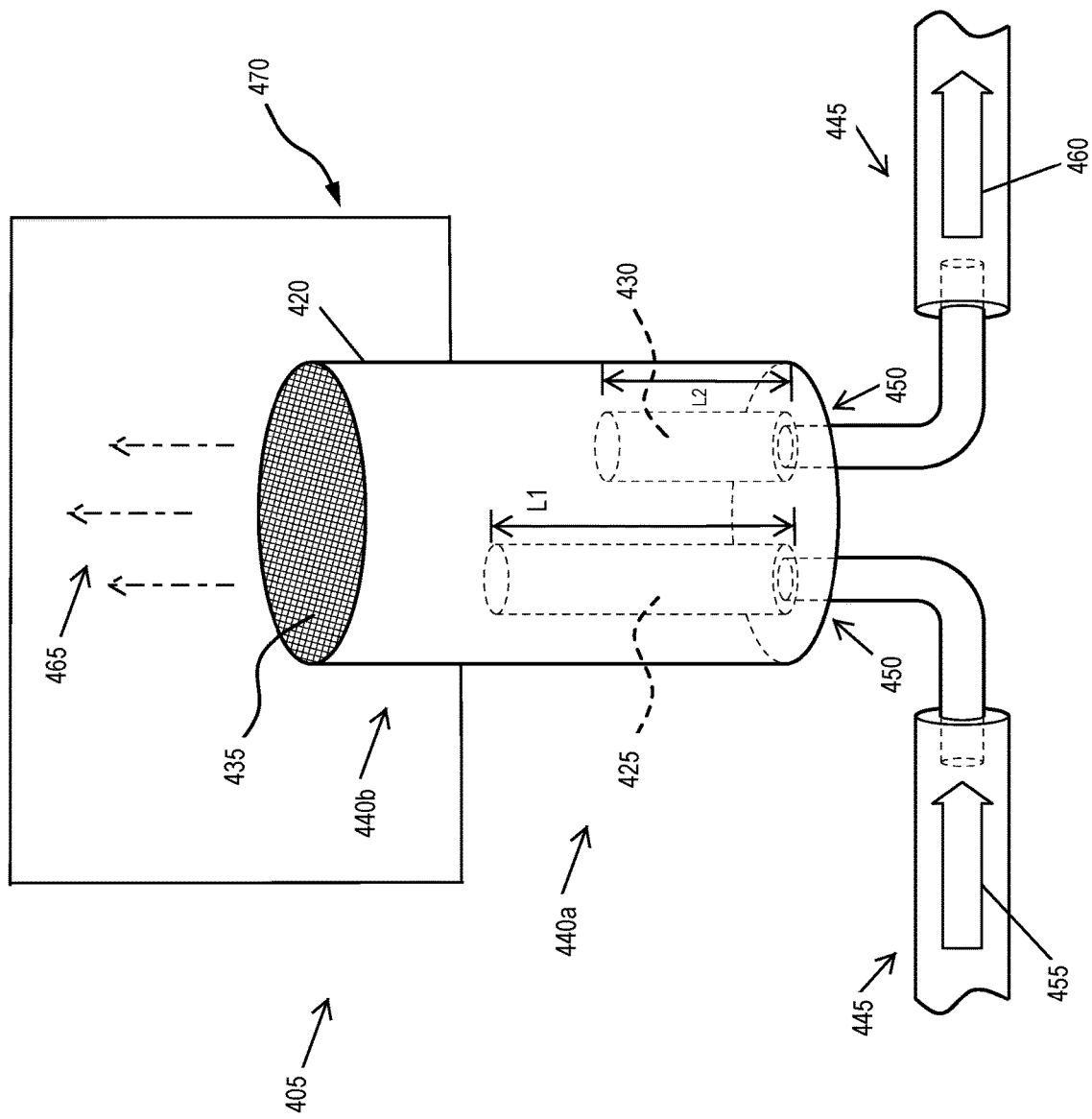
FIG. 6 illustrates an exemplary embodiment of a filter for the warmer pouch of FIG. 4 in accordance with the present disclosure.

As shown in FIGS. 4-6, the warmer pouch 224 may include a filter 405 in-line with warmer pouch 224, e.g., coupled to an inlet of the warmer pouch 224. For example, dialysate flowing to the patient through the warmer pouch 224 from dialysate bags 122 may flow through the filter 405, e.g., before entering the warmer pouch 224. In embodiments, the filter 405 may be coupled to the warmer pouch 224 directly or indirectly by tubing. The filter 405 may filter out air content in the dialysate flow. In some embodiments, a filter may be a hydrophobic filter, e.g., having a hydrophobic membrane 435 in the fluid path in the area where a positive internal pressure may allow the air content to escape from the system as the dialysate flow is flowed (e.g., pumped) through the system 100, without allowing additional air or other gases to enter the dialysate flow. In some embodiments, the filter 405 may be a container 420, e.g., a cylindrical container, having an inlet 425 for receiving dialysate and air, and an outlet 430 for flowing dialysate with air content filtered out of the dialysate. It is understood that the container 420 may be any configuration, e.g., size and/or shape, to filter air content from dialysate.

The inlet 425 and the outlet 430 may extend into the container 420 from a lower portion 440a, and/or one or more bottom openings 450 in the container 420. In embodiments, o-rings or other seals may be disposed between the tubing 445 and the openings 450 to minimize leakage. The inlet 425 and the outlet 430 of the filter 405 may be coupled to system tubing 445, e.g., dialysate bag lines and/or warmer pouch lines, so that the dialysate may flow from the dialysate bags through the warmer pouch 224 for heating before delivery to the patient. In some embodiments, the inlet 425 and the outlet 430 of a filter 405 may be disposed in a lower portion 440a of the container 420 of the filter 405, so that any air content and dialysate may separate by gravity. For example, air content may flow from tubing 445 to an upper portion 440b as indicated by arrow 455, in a vicinity where the hydrophobic membrane 435 may be disposed (e.g., towards the upper portion 440b of the container 420), and the dialysate may remain in the lower portion 440a of the container 420, as described below. In some embodiments, the inlet 425 and the outlet 430 of the filter 405 may have the same length "L," although in other embodiments, the inlet 425 and the outlet 430 may be different lengths within the container. For example, the inlet 425 may have a length "L1," which may be longer, than the outlet 430 having a length "L2," e.g., the inlet 425 may extend further in the container 420 than the outlet 430, so that positive pressure may allow the dialysate to flow through the filter 405 to the outlet 430, as shown by arrow 460, and any air content may be exposed at the upper portion 440b of the container 420 near the hydrophobic membrane 435 for flowing out of the hydrophobic membrane 435 in the direction shown by arrows 465.

The filter 405 may act to trap air or other gases, thereby preventing or significantly reducing the gases from flowing through the system to the patient, e.g., including through the warmer pouch 224 when a filter 405 is located in-line before the inlet of the pouch. Thus, dialysate with air content removed or significantly reduced may be flowed through the warmer pouch 224, and may be delivered to the patient, reducing or eliminating the need to drain or purge dialysate due to undesired air content. As described, to minimize or eliminate air content in the dialysate flow, the filter 405 may be disposed at the inlet of the warmer pouch 224 (indicated by arrow 410), thus also minimizing the impact of air content on the heater system performance. Thus, as the heating elements act on the dialysate flowing through the warmer pouch 224, with the air content reduced or eliminated, the dialysate may be more consistently heated and may prevent overheating of the dialysate and thus additional wasted dialysate.

Dialysate may flow through the filter 405 at the inlet of the warmer pouch 224, and may flow through an extended flow path in the warmer pouch 224. For example, a flow path may be a tortuous, or circuitous, pathway, so that the dialysate may flow at a constant rate into the patient, and may heat to the desired predetermined temperature while flowing through the tortuous flow path of the warmer pouch 224. The dialysate may flow from the warmer pouch into the patient at an outlet of the warmer pouch 224, indicated at arrow 415. Although the flow path shown in FIG. 4 is somewhat circular, any labyrinth of circuitous flow path may be incorporated in the warmer pouch 224 to ensure a constant flow of the dialysate so that the dialysate temperature is heated to the predetermined temperature before flowing into the patient.

In some embodiments, the filter 405 may include a negative pressure chamber disposed on at least a portion of the exterior of the filter 405 in the area of the membrane 435, as indicated by reference numeral 470. However, it is understood that a negative pressure chamber may be any configuration, including shape and size, and the filter 405 may be partially or wholly enclosed. It is also understood that the negative pressure chamber may include any known mechanism for ventilation or vacuum to generate a lower pressure, so that any air content may flow from the container 420 through the membrane 435.

As air content and dialysate flow into the filter 405 e.g., as shown by arrow 455 and as described above, gravity may allow the dialysate and the air content to separate, so that the air content is disposed in an upper portion 440b towards the hydrophobic membrane 435 while the dialysate remains in the lower portion 440a of the container 420. When the exterior of the filter 405 is in a negative pressure state, for example, caused by a negative pressure chamber, the air content may flow from an area of higher pressure (e.g., inside the container 420) to the lower pressure area (e.g., the negative pressure chamber). A pressure drop across the membrane 435 may therefore allow air content to flow across the membrane 435, as shown by arrows 465, separating the air content from the dialysate. When placed at an inlet of the warmer pouch 224, the filter 405 may act to prevent the air content from flowing with the dialysate into the warmer pouch 224. For example, air content may be filtered out by the filter 405 prior to flowing through the warmer pouch 224.

As described above, the dialysis machine 200 may include in-line heating of the dialysate via the warmer pouch 224. The filter 405, including the hydrophobic membrane 435, may also be disposed in-line with the warmer pouch 224, which may always be in a positive pressure relative to ambient on the outlet of the pump and between the pump and the patient.

In some embodiments, a second filter 405 may be placed at the outlet or on the outlet side of the warmer pouch 224 instead of or in addition to the inlet or on the inlet side of the warmer pouch 224. The filter 405 and membrane 435 may act as a redundant air content purging mechanism at the outlet of the warmer pouch 224, before flowing into the patient.

In embodiments, the filter 405 may augment (but not replace) air sensors 340 in the dialysis machine. Air sensors within the dialysis machine 200 may still be used to detect larger volumes of air, such as a disconnected/misconnected line, leak, and the like. In some instances, a larger volume of air detected in the dialysis system 100 may result in an alarm to alert the patient or other medical professional, and the dialysis treatment may be paused and/or stopped. Although a smaller volume of air may still be delivered to the patient during treatment, it may be advantageous to minimize air delivery by including a filter 405 to reduce the potential of patient pain (e.g., shoulder and/or abdominal pain or cramping) resulting from air build-up in the patient during treatment. Thus, including a filter 405 to minimize and/or eliminate air content before flowing to the patient, including for example before flowing through the warmer pouch 224, may be advantageous in improving patient care during treatment.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A dialysis system for conducting a dialysis treatment, comprising:
    a dialysis machine for transferring dialysate to a patient from a dialysate bag, the dialysis machine including a housing having an opening formed therein;
    a warmer pouch partially insertable into the opening formed in the housing, the warmer pouch being operatively coupled to tubing so that dialysate is moved through the warmer pouch when the warmer pouch is positioned in the opening formed in the housing, the warmer pouch arranged and configured to receive dialysate from the dialysate bag at a first temperature and arranged and configured to transfer dialysate to the patient at a predetermined temperature before flowing into the patient, the predetermined temperature being greater than the first temperature, the dialysate flowing from the dialysate bag through the warmer pouch and into the patient via tubing; and
    a filter positioned on the warmer pouch such that the filter remains outside of the dialysis machine when the warmer pouch is inserted into the opening formed in the housing, the filter configured to filter out air content from the dialysate;
    wherein the filter includes a container having an inlet for the dialysate to flow into the container and an outlet for the dialysate to flow out of the container after being filtered, the inlet arranged and configured to extend into the container by a length L1, the outlet arranged and configured to extend into the container by a length L2, length L1 being longer than length L2 so that the inlet extends farther into the container than the outlet.

2. The dialysis system according to claim 1, wherein the filter is a hydrophobic filter.

3. The dialysis system according to claim 1, wherein the outlet of the filter is coupled to an inlet of the warmer pouch, such that the air content is removable before flowing through the warmer pouch.

4. The dialysis system according to claim 1, wherein the filter includes a hydrophobic membrane.

5. The dialysis system according to claim 4, wherein a negative pressure chamber is disposed exterior to the hydrophobic membrane, such that the air content is flowable to the negative pressure chamber from an area of positive pressure in the filter.

6. The dialysis system according to claim 3, further comprising a second filter coupled to an outlet of the warmer pouch.

7. The dialysis system according to claim 1, wherein the filter is coupled to the warmer pouch by the tubing connecting to the dialysate bag for transferring the dialysate to the patient.

8. The dialysis system according to claim 1, wherein the filter includes a membrane for filtering out the air content.

9. The dialysis system according to claim 8, wherein the inlet and the outlet are disposed through a lower portion of the container, and the membrane is disposed on an upper portion of the container.

10. A dialysis system for conducting a dialysis treatment, comprising:
    a dialysis machine for transferring dialysate to a patient from a dialysate bag, the dialysis machine including a housing having an opening formed therein;
    a warmer pouch partially insertable into the opening formed in the housing, the warmer pouch being operatively coupled to tubing so that dialysate is moved through the warmer pouch when the warmer pouch is positioned in the opening formed in the housing, the warmer pouch arranged and configured to receive dialysate from the dialysate bag at a first temperature and arranged and configured to transfer dialysate to the patient at a predetermined temperature before flowing into the patient, the predetermined temperature being greater than the first temperature, the dialysate flowing from the dialysate bag through the warmer pouch and into the patient via tubing; and
    a filter positioned on the warmer pouch such that the filter remains outside of the dialysis machine when the warmer pouch is inserted into the opening formed in the housing, the filter configured to filter out air content from the dialysate.

11. The dialysis system according to claim 10, wherein the filter is a hydrophobic filter.

12. The dialysis system according to claim 10, wherein an outlet of the filter is coupled to an inlet of the warmer pouch, such that the air content is removable before flowing through the warmer pouch.

13. The dialysis system according to claim 10, wherein the filter includes a hydrophobic membrane.

14. The dialysis system according to claim 13, wherein a negative pressure chamber is disposed exterior to the hydrophobic membrane, such that the air content is flowable to the negative pressure chamber from an area of positive pressure in the filter.

15. The dialysis system according to claim 12, further comprising a second filter coupled to an outlet of the warmer pouch.

16. The dialysis system according to claim 10, wherein the filter is coupled to the warmer pouch by the tubing connecting to the dialysate bag for transferring the dialysate to the patient.

17. The dialysis system according to claim 10, wherein the filter includes a container having an inlet for the dialysate to flow into the container, an outlet for the dialysate to flow out of the container after being filtered, and a membrane for filtering out the air content.

18. The dialysis system according to claim 17, wherein the inlet and the outlet of the container are disposed through a lower portion of the container, and the membrane is disposed on an upper portion of the container.

19. The dialysis system according to claim 17, wherein the inlet is arranged and configured to extend into the container by a length L1, the outlet is arranged and configured to extend into the container by a length L2, length L1 being longer than length L2 so that the inlet extends farther into the container than the outlet.

* * * * *